(12) United States Patent
Kakuta et al.

(10) Patent No.: US 7,531,358 B2
(45) Date of Patent: May 12, 2009

(54) METHOD OF QUANTIFYING SURFACTANT

(75) Inventors: Masaya Kakuta, Shizuoka (JP); Masahiko Tanikawa, Tokyo (JP); Naoyoshi Kuroyanagi, Tokyo (JP); Yoshiyuki Endo, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 38 days.

(21) Appl. No.: 10/475,163

(22) PCT Filed: Apr. 17, 2002

(86) PCT No.: PCT/JP02/03821

§ 371 (c)(1),
(2), (4) Date: May 11, 2004

(87) PCT Pub. No.: WO02/086492

PCT Pub. Date: Oct. 31, 2002

(65) Prior Publication Data

US 2004/0185572 A1    Sep. 23, 2004

(30) Foreign Application Priority Data

Apr. 17, 2001    (JP)    ............................. 2001-118510

(51) Int. Cl.
*G01N 33/00*    (2006.01)
*A61K 45/00*    (2006.01)
*C12Q 1/68*    (2006.01)

(52) U.S. Cl. .................... 436/86; 436/119; 436/131; 424/85.1; 435/6

(58) Field of Classification Search ................ 436/131, 436/119, 86; 424/85.1; 435/6
See application file for complete search history.

(56) References Cited

U.S. PATENT DOCUMENTS

| 5,252,458 A | * | 10/1993 | Liav et al. | ....................... 435/5 |
| 5,856,298 A | | 1/1999 | Strickland | |
| 6,120,761 A | * | 9/2000 | Yamazaki et al. | .......... 424/85.1 |
| 6,617,165 B1 | * | 9/2003 | Opitz et al. | .................... 436/55 |
| 2002/0177139 A1 | * | 11/2002 | Greenfield et al. | ............. 435/6 |

FOREIGN PATENT DOCUMENTS

| JP | S63-146826 A | 6/1988 |
| JP | H8-151398 | 6/1996 |

(Continued)

OTHER PUBLICATIONS

Ghebeh, Hazem, Development of an Assay for the Measurement of the Surfactant Pluronic F-68 in Mammalian Cell Cuture Medium, Analytical Biochemistry, vol. 262, 39-44.*

(Continued)

*Primary Examiner*—Jill Warden
*Assistant Examiner*—Lore Ramillano
(74) *Attorney, Agent, or Firm*—Browdy and Neimark, PLLC

(57) ABSTRACT

A method of quantifying an ethylene oxide based nonionic surfactant in a sample containing a physiologically active protein, characterized in that quantitation is performed by colorimetry, in particular, a method of quantifying an ethylene oxide based nonionic surfactant in a sample containing a physiologically active protein, characterized in that an ammonium thiocyanate/cobalt nitrate reagent (CoSCN reagent) is added to said sample solution and the resulting cobalt thiocyanate complex is quantified by absorbance measurement.

12 Claims, 2 Drawing Sheets

FOREIGN PATENT DOCUMENTS

| | | |
|---|---|---|
| JP | H8-506023 | 7/1996 |
| JP | 2001-099835 | 4/2001 |
| WO | WO 99/39196 A1 | 8/1999 |

OTHER PUBLICATIONS

Crabb et al., A Determination of the Apparent Molar Absorption Coefficients of the Cobalt Thiocyanate Complexes of Nonylphenol Ethylene Oxide Adducts, Mar. 28, 1968, The Journal of the American Oil Chemists' Society, vol. 45, 611-615.*

"A Compendium of the 12$^{th}$ rev. Japanese Pharmacopoeia, B-639 (polysorbate 20) and D-891 (polysorbate 80)", Hirokawa Shoten. 1991.

Adachi, et al., "Atomic Absorption Spectrophotometric Determination of Polyoxyethylene-type Nonionic Surfactants in Water", Eisei Kagaku. 1983, vol. 29, No. 3, 123-129.

Favretto, et al., "An Improved Method for the Spectrophotometric Determination of Polyoxyethylene Non-Ionic Surfactants in Waters as Potassium Picrate Active Substances in Presence of Cationic Surfactants", Intern. J. Environ. Anal. Chem. 1983, vol. 14, 201-214.

Garti, et al., "Analyses of Polyglycerol Esters of Fatty Acids Using High Performance Liquid Chromatography", Journal of Liquid Chromatography. 1981, vol. 4, No. 7, 1173-1194.

Garti, et al., "Analysis of Sorbitan Fatty Acid Esters by HPLC", Journal of American Oil Chemists Society. Jun. 1983, vol. 60, No. 6 1151-1154.

Greff, et al., "A colorimetric Method for the Determination of Part/Million of Nonionic Surfactants", The Journal of the American Oil Chemists' Society. Mar. 1965, vol. 42, 180-185.

Kudoh, et al., "Determination of Trace Amounts of Alcohol and Alkyl-phenol Ethoxylates by High-Performance Liquid Chromatography with Fluorimetric Detection", Journal of Chromatography. 1984, vol. 287, 337-344.

London Her Majesty's Stationary Office, "British Pharmacopoeia", 1993, vol. 1, 525.

Murai, S., "Spectrometric Determination of Polyoxyethylene Nonionic Surfactants with Thiocyanate-iron (III)", 1984, vol. 33, T18-T21.

Tanaka, et al, "Determination of Nonionic Surfactant in River Water and Sediment by Hydrogen Bromide Fission Method", Yamanashi Institute of Public Health. 1984, vol. 7, No. 5, 294-300.

Wang, et al., "Gas Chromatographic Separation of Long-Chain Fatty Nitriles and Lon-Chain Acid Amides", Journal of American Oil Chemists Society. Mar. 1984, vol. 61, No. 3, 581-583.

Wickbold, R., Tenside Detergents. 1972, vol. 9, No. 4, 173-177.

D. L. McKean et al., "Determination of Polysorbate in Ascites Fluid from a Premature Infant", *Journal of Analytical Toxicology*, vol. 9, pp. 174-176, Jul./Aug. 1985.

Seikagaku Jiten, 1988, First Edition, 8th Issue, p. 30. [Acetone-dried preparation].

* cited by examiner

Standard solution of polysorbate 20 rG-CSF injection

Water (blank)

METHOD OF QUANTIFYING SURFACTANT

TECHNICAL FIELD

The present invention relates to a method of quantifying ethylene oxide based nonionic surfactants such as polysorbate in protein-containing samples such as protein-containing formulations.

BACKGROUND ART

Advances in genetic recombination technology have allowed a variety of protein formulations to be offered in consistent amounts of supply. In order to stabilize, those formulations are provided either as a form where freeze-dried powder of protein component is packaged separately from a liquid diluent for dissolving it upon using, or as a protein solution formulation having an additive added to improve its stability.

Such protein containing formulations in some cases contain nonionic surfactant of polysorbates with a view to preventing protein adsorption on the container and stabilizing. For example, a granulocyte colony stimulating factor (G-CSF) formulation containing polysorbates as a stabilizer has been disclosed (JP 63-146826 A).

Polysorbates are polyoxyethylene sorbitan fatty acid esters and, depending on the species of the fatty acid ester, are designated 20 (monolaurate), 40 (monopalmitate), 60 (monostearate) and 80 (monooleate), each bonding to a polymer comprising about 20 moles of ethylene oxide units. Taking polysorbate 20 as an example, it can be produced by the following method:

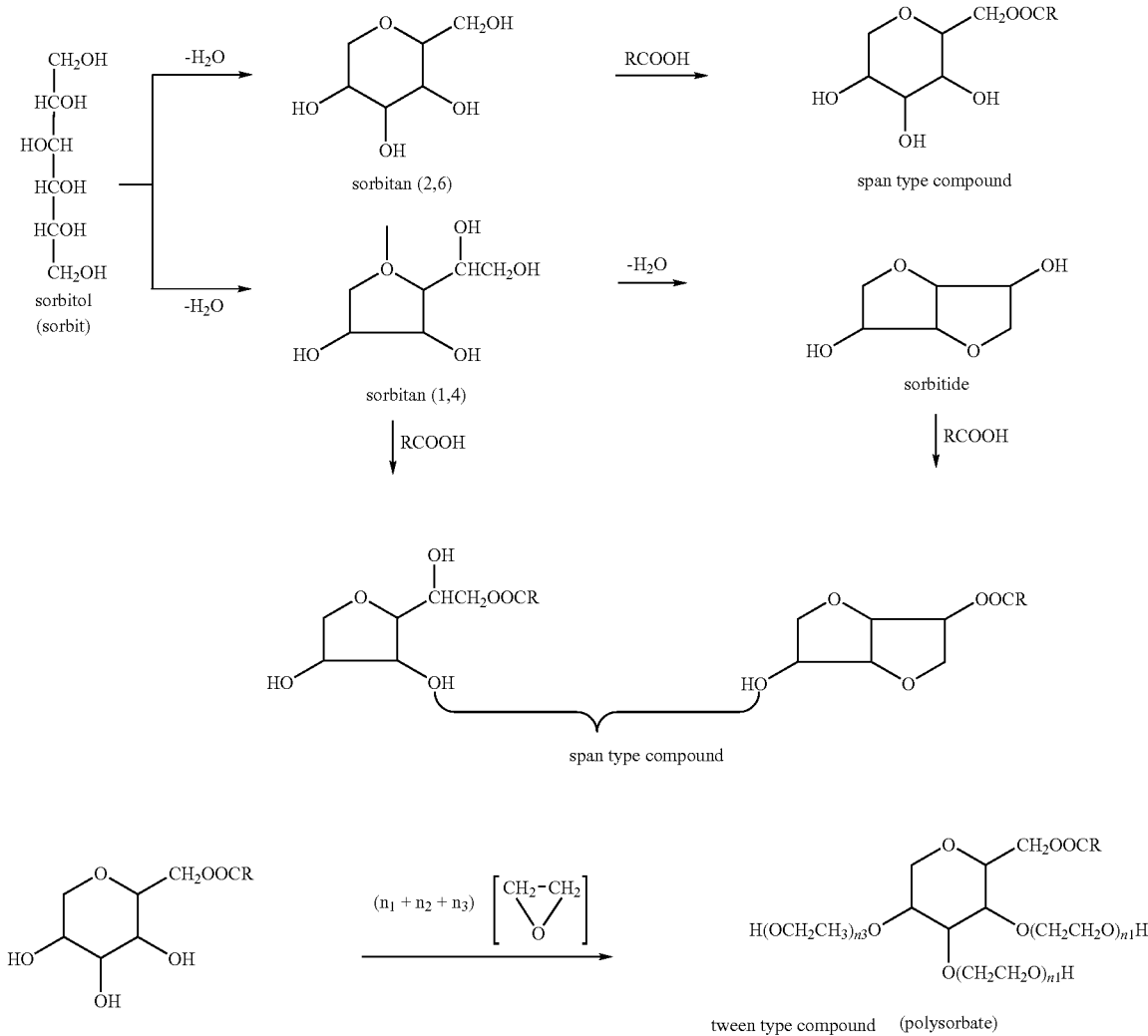

Briefly, sorbitol is subjected to intramolecular dehydration to make sorbitan (2,6-type and 1,4-type), which in turn is reacted with lauric acid in the presence of NaOH as a catalyst to make a fatty acid ester, and the fatty acid esters then treated with ethylene oxide. In polysorbate 20, 1 mole of sorbitan monolaurate is bound to about 20 moles of ethylene oxide, and the molecule does not have a single structure. Polysorbates 20 and 80 are used most preferably in formulations containing proteins such as erythropoietin (EPO) and granulocyte colony stimulating factor (G-CSF).

Polysorbates are generally added to protein formulations-in very small-amounts of 0.001-3%, and in order to control the quality of the protein formulations, it is necessary to establish methods of verifying and quantifying such small amounts of polysorbates. Polysorbate 80 currently used in EPO formulations are not highly effective in preventing adsorption if its concentration is too low; on the other hand, if its concentration is too high, it promotes the decomposition of the protein. It is therefore required that the amounts of polysorbates in protein formulations be measured accurately.

The following methods may be employed to quantify polysorbates.

1) High performance liquid chromatography (HPLC): An alkyl ether of poly(ethylene oxide) is fluorescently labeled with 1-anthroylnitrile and thereafter analyzed on a reverse-phase column (M. Kudoh et al., J. Chromatogr., 287:337, 1984); in other methods, detection at a low wavelength of 220 nm is utilized with direct analysis on a reversephase column (RP18) (N. Garti et al., J. Am. Oil Chem. Soc., 60:1151, 1983) or a normal phase column (N. Garti et al., J. Liq. Chromatogr., 4:1173, 1981).
2) Gas chromatography (GC): A fatty acid produced by acid hydrolysis is converted to a methyl ester which is then analyzed (C. N. Wang et al., J. Am. Oil Chem. Soc., 61:581, 1983); alternatively, hydrobromic acid is allowed to act on the sample and the generated 1,2-dibromoethane is analyzed (Hisashi Tanaka et al., Suishitsu Odaku Kenkyu, 7:294, 1984).
3) Wickbold's method: After foam concentration, a Dragendorff reagent is added to form a precipitate, which is then dissolved and subjected to a potentiometric titration using pyrrolidine dithiocarbamate (R. Wickbold, Tenside Deterg., 9:173, 1972, etc.).
4) Frameless atomic absorption spectrometry: Cobalt in a combined complex of polysorbate and cobalt thiocyanate-ammonium is analyzed by atomic absorption spectrometry (A. Adachi et al., Eisei Kagaku, 29:123, 1983).
5) Colorimetry: A combined complex formed of the ethylene oxide portion of polysorbate and cobalt thiocyanate-ammonium is measured by absorbance (at maximum wavelength) (R. A. Greff et al., J. Am. Oil Chem. Soc., 42:180, 1965, etc.); other methods include a similar use of a complex with iron(III) thiocyanate (Shoji Murai: Bunseki Kagaku, 33: T18, 1984), as well as a method in which potassium ions are coordinated to polysorbate and an ion pair consisting of the potassium ion and the picrate ion is extracted with dichloroethane and subjected to colorimetry (L. Favretto et al., Intern. J. Environ. Anal. Chem., 14:201, 1983).

Among the methods mentioned above, the colorimetry using the cobalt thiocyanate complex has high sensitivity, is easy to perform, does not require any special equipment or reagents, and features the widest scope of applicability. In addition, this method is described as an identification test for polysorbate 80 in Japanese Pharmacopoeia (A Compendium of the 12$^{th}$ rev. Japanese Pharmacopoeia, B-639 (polysorbate 20) and D-891 (polysorbate 80), Hirokawa Shoten) and as an identification test for polysorbate 20 in British Pharmacopoenia (British Pharmacopoeia 1993, Vol.1, 525, London Her Majesty's Stationary Office) . Hence, the colorimetric approach using the cobalt thiocyanate complex is considered to be most suited as a method of quantifying polysorbates in drugs. Briefly, the method comprises adding an ammonium thiocyanate/cobalt nitrate reagent to an aqueous solution of the sample, further adding an organic solvent such as chloroform or dichloromethane to the solution, mixing the ingredients by shaking to transfer the cobalt thiocyanate complex to the organic solvent layer, and performing colorimetry of the cobalt thiocyanate complex.

However, if a sample solution containing a protein is tested by the same method, a protein aggregate may sometimes form between the water layer and the organic solvent layer, and lower the extraction rate of the polysorbate, eventually making it impossible to achieve accurate quantitation.

It is therefore required to develop a method by which the contents of polysorbates in protein containing solution samples can be determined in a simple and accurate manner.

DISCLOSURE OF THE INVENTION

The present inventors found that when an attempt was made to quantify polysorbates and other ethylene oxide based nonionic surfactants in protein containing samples, the above object could be attained by performing absorbance measurement on the resulting cobalt thiocyanate complex. The present invention has been accomplished on the basis of this finding.

Briefly, the present invention provides the following:
(1) A method of quantifying an ethylene oxide based nonionic surfactant in a sample containing a physiologically active protein, characterized in that quantitation is performed by colorimetry using an ammonium thiocyanate/cobalt nitrate reagent (CoSCN reagent).
(2) The method of quantifying an ethylene oxide based nonionic surfactant in a sample containing a physiologically active protein as set forth in (1) above, characterized in that an ammonium thiocyanate/cobalt nitrate reagent (CoSCN reagent) is added to said sample solution and the resulting cobalt thiocyanate complex is quantified by absorbance measurement.
(3) The method as set forth in (2) above which comprises the following steps:
1) adding the CoSCN reagent to the sample containing a physiologically active protein;
2) adding a non-aqueous organic solvent to the sample and shaking the mixture;
3) collecting the obtained non-aqueous organic solvent layer and quantifying the cobalt thiocyanate complex-by absorbance measurement; and
4) calculating the amount of the ethylene oxide based nonionic surfactant from the amount of the cobalt thiocyanate complex.
(4) The method as set forth in (2) above, which comprises adding an aqueous organic solvent to the sample containing a physiologically active protein, thereby forming a precipitate of the physiologically active protein, removing the precipitate, and adding the CoSCN reagent to the cleared sample.
(5) The method as set forth in (4) above which comprises the following steps:
1) adding an aqueous organic solvent to the sample containing a physiologically active protein, thereby forming a precipitate of the physiologically active protein;
2) adding the CoSCN reagent to the cleared sample;

3) adding a non-aqueous organic solvent to the sample and shaking the mixture;
4) collecting the obtained non-aqueous organic solvent layer and quantifying the cobalt thiocyanate complex by absorbance measurement; and
5) calculating the amount of the ethylene oxide based nonionic surfactant from the amount of the cobalt thiocyanate complex.

(6) The method as set forth in (4) or (5), wherein the aqueous organic solvent is acetone.

(7) The method as set forth in any one of (4)-(6) above, wherein the precipitate is removed by filtration or centrifugation.

(8) The method as set forth in (2) above, wherein a proteinase is added to the sample containing a physiologically active protein, thereby digesting the physiologically active protein, and thereafter adding the CoSCN reagent to the sample.

(9) The method as set forth in (8) above which comprises the following steps:
1) adding a proteolytic enzyme to the sample containing a physiologically active protein, thereby digesting the physiologically active protein;
2) adding the CoSCN reagent to the sample obtained in 1);
3) adding a non-aqueous organic solvent to the sample and shaking the mixture;
4) collecting the obtained non-aqueous organic solvent layer and quantifying the cobalt thiocyanate complex by absorbance measurement; and
5) calculating the amount of the ethylene oxide based nonionic surfactant from the amount of the cobalt thiocyanate complex.

(10) The method as set forth in (8) or (9) above, wherein the proteolytic enzyme is proteinase K.

(11) The method as set forth in (1) or (2) above, characterized in that a protein included in the sample containing the physiologically active protein is added to a standard solution at the same concentration as in the sample, and a standard curve is constructed.

(12) The method as set forth in (11) above which comprises the following steps:
1) adding the CoSCN reagent to the sample containing a physiologically active protein;
2) adding a non-aqueous organic solvent to the sample and shaking the mixture;
3) collecting the obtained non-aqueous organic solvent layer and quantifying the cobalt thiocyanate complex by absorbance measurement;
4) adding to a standard solution a protein included in the sample containing the physiologically active protein at the same concentration as in the sample, constructing a standard curve, and correcting the amount of the cobalt thiocyanate complex in the sample on the basis of said standard curve; and
5) calculating the amount of the ethylene oxide based nonionic surfactant from the amount of the cobalt thiocyanate complex.

(13) The method as set forth in any one of (1)-(12) above, wherein the ethylene oxide based nonionic surfactant is polysorbate and/or polyoxyethylene polyoxypropylene glycol.

(14) The method as set forth in (13) above, wherein the polysorbate is polysorbate 20 and/or 80.

(15) The method as set forth in any one of (1)-(14) above, wherein the non-aqueous organic solvent is dichloromethane.

(16) The method as set forth in any one of (2)-(15) above, wherein the addition of the CoSCN reagent is accompanied by the addition of a salt before measurement.

(17) The method as set forth in (16) above, wherein the salt is potassium chloride or sodium chloride.

(18) The method as set forth in any one of (1)-(17) above, wherein the sample containing a physiologically active protein is a concentrated protein formulation.

(19) The method as set forth in (18) above, wherein the physiologically active protein is contained in the sample in an amount of at least 8 µg/ml.

(20) The method as set forth in any one of (1)-(19) above, wherein the physiologically active protein is a hemopoietic factor protein.

(21) The method as set forth in (20) above, wherein the physiologically active protein is erythropoietin.

(22) The method as set forth in (20) above, wherein the physiologically active protein is a granulocyte colony stimulating factor.

(23) The method as set forth in any one of (1)-(19) above, wherein the physiologically active protein is an antibody.

(24) A method of quantifying an additive in a sample containing a physiologically active protein by adding a colorimetric reagent to the sample and quantifying by absorbance measurement the product formed between the calorimetric reagent and the additive in the sample containing a physiologically active protein, further including any one of the following steps:
A) adding an aqueous organic solvent to the sample containing a physiologically active protein, thereby forming a precipitate of the physiologically active protein, removing the precipitate, and thereafter adding the colorimetric reagent to the cleared sample;
B) adding a proteolytic enzyme, thereby digesting the protein in the sample, and thereafter adding the colorimetric reagent; or
C) adding to a standard solution a protein of the same kind in the same amount as the protein contained in the sample and constructing a standard curve.

BEST MODE FOR CARRYING OUT THE INVENTION

Figure 1:
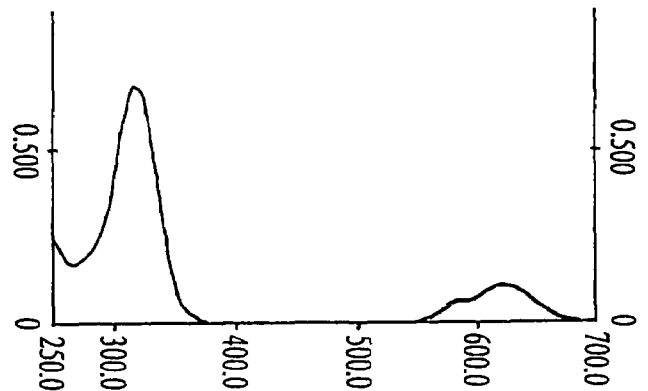
FIG. 1 shows absorption spectra (250-700 nm) for the dichloromethane layer as obtained by mixing a standard solution of polysorbate 20 (0.5 mg/2 ml), a sample solution or water (blank) with a CoSCN reagent in accordance with the standard procedure.
Figure 1:
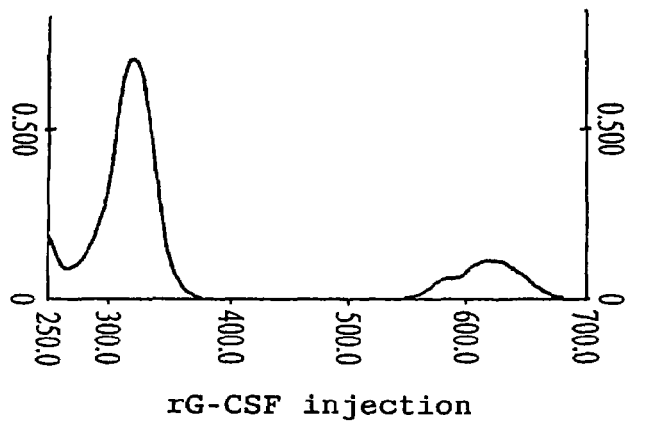
Figure 1:
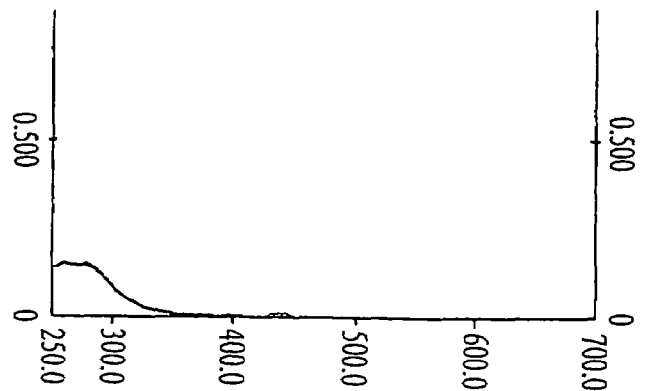

Ethylene oxide based nonionic surfactants to be measured by the method of the invention include polyoxyethylene sorbitan fatty acid esters (polysorbates), polyoxyethylene hardened castor oil, polyoxyethylene glycerol fatty acid esters, polyoxyethylene alkyl ethers, polyoxyethylene polyoxypropylene glycol, polyoxyethylene alkyl allyl ethers, etc. and polysorbates and polyoxyethylene polyoxypropylene glycol are preferred. Polysorbates include polysorbate 20, 21, 40, 60, 65, 80, 81, 85, etc. and polysorbate 20 and/or 80 is preferred. Examples of polyoxyethylene polyoxypropylene glycol include poloxamers (e.g. Pluronic F-68 (registered trademark)).

In the method of the invention, the ethylene oxide based nonionic surfactant in a sample containing a physiologically active protein is determined by colorimetry. Techniques of colorimetry preferred in the invention include observation of colors with the naked eye and measurement with a spectrophotometer, and preferably quantitation is performed by measuring absorbance with a spectrophotometer.

In a preferred embodiment of the invention, an ammonium thiocyanate/cobalt nitrate reagent (CoSCN reagent) is added to a sample solution containing a physiologically active protein, and the resulting cobalt thiocyanate complex is quantified by absorbance measurement to determine the amount of the ethylene oxide based nonionic surfactant in a sample containing the physiologically active protein.

In a preferred embodiment of the invention, the method of the invention comprises the following steps:
1) adding the CoSCN reagent to the sample containing a physiologically active protein;
2) adding a non-aqueous organic solvent to the sample and shaking the mixture;
3) collecting the obtained non-aqueous organic solvent layer and quantifying the cobalt thiocyanate complex by absorbance measurement; and
4) calculating the amount of the ethylene oxide based nonionic surfactant from the amount of the cobalt thiocyanate complex.

The method of the invention starts with adding the ammonium thiocyanate/cobalt nitrate reagent (CoSCN reagent) to a sample containing a water-soluble physiologically active protein.

The CoSCN reagent is prepared by dissolving ammonium thiocyanate ($NH_4SCN$) and cobalt nitrate ($Co(NO_3)_2/6H_2O$) in water. For instance, 17.4 g of ammonium thiocyanate and 2.8 g of cobalt nitrate are dissolved in water to make 100 ml.

Subsequently, a non-aqueous organic solvent is added to the solution, the mixture is shaken, and the non-aqueous organic solvent layer is collected. A cobalt thiocyanate complex (blue in color), which is formed of the CoSCN reagent and the ethylene oxide in the ethylene oxide based surfactant, moves into the non-aqueous organic solvent. Since the distribution ratio of the cobalt thiocyanate complex into the non-aqueous organic solvent layer did not vary with the amount of the added non-aqueous organic solvent, the amount of the non-aqueous organic solvent can be set at appropriate values that will provide concentrations preferred for absorbance measurement.

Non-aqueous organic solvents that are to be used in extracting the cobalt thiocyanate complex include dichloromethane, 1,2-dichloroethane, chloroform, toluene and benzene, with dichloromethane and 1,2-dichloroethane being preferred, and dichloromethane being the most preferred. These organic solvents are preferably used after adding water in a separating funnel, mixing them and separating a water-saturated mass. Water-saturated dichloromethane is most preferably used.

When salts such as potassium chloride and sodium chloride are added during extraction with the non-aqueous organic solvent, the effect of salting out was found to help provide more effective extraction. The amount of the salts to be added is at least 5%, preferably 10-50%, of the sample containing a physiologically active protein.

Measurement can be performed by the preparing a standard solution of an ethylene oxide based surfactant (e.g. polysorbate), constructing a calibration curve, measuring the cobalt thiocyanate complex in a similar way, and determining the amount of the ethylene oxide based surfactant in the sample containing a physiologically active protein on the basis of that measurement.

The theory behind the measurement according to the invention is forming a blue combined complex of the CoSCN reagent and ethylene oxide (cobalt thiocyanate complex), extracting it into the non-aqueous organic solvent layer, preferably a dichloromethane layer, and measuring it by absorbance measurement. The absorption spectrum shows absorption maxima in the neighborhood of 320 nm and 620 nm. Quantitation can be realized with a spectrophotometer (e.g. DU 640: BECKMAN) by measuring the absorbance in the neighborhood of 320 nm where the higher absorbance is observed.

In the method of the invention, depending on the kind of the physiologically active protein, a protein aggregate may occasionally form between the water layer and the organic solvent layer, eventually lowering the extraction rate of the ethylene oxide based nonionic surfactant. According to the invention, that problem could be solved by either one of the following methods:
A) adding an aqueous organic solvent to the sample containing a physiologically active protein, thereby forming a precipitate of the physiologically active protein, removing the precipitate, and thereafter adding the CoSCN reagent to the cleared sample;
B) adding a proteolytic enzyme, thereby digesting the protein in the sample, and thereafter adding the CoSCN reagent; or
C) adding to a standard solution a protein of the same kind in the same amount as the protein contained in the sample and constructing a standard curve.

Each embodiment is described below in detail. In the following description, all embodiments assume the use of polysorbate as the ethylene oxide based nonionic surfactant.

Embodiment A

In a preferred embodiment of the invention, an aqueous organic solvent is added to the sample containing a physiologically active protein, thereby forming a precipitate of the physiologically active protein, said precipitate is removed from the sample, and the CoSCN reagent is added to the cleared sample.

In a preferred embodiment of the invention, the method of the invention comprises the following steps:
1) adding an aqueous organic solvent to the sample containing a physiologically active protein, thereby forming a precipitate of the physiologically active protein;
2) removing said precipitate;
3) adding the CoSCN reagent to the cleared sample;
4) adding a non-aqueous organic solvent to the sample and shaking the mixture;
5) collecting the obtained non-aqueous organic solvent layer and quantifying the cobalt thiocyanate complex contained in it by absorbance measurement; and
6) calculating the amount of the ethylene oxide based nonionic surfactant from the amount of the cobalt thiocyanate complex.

The aqueous organic solvent is preferably acetone, ether or alcohol, with acetone being particularly preferred. The amount of addition of the aqueous organic solvent is preferably at least 1 ml, more preferably at least 1.5 ml, per ml of the sample. It is more preferred to extract the polysorbate after washing the removed precipitate 1-5 times with the aqueous organic solvent.

In removing the precipitate of the physiologically active protein formed by adding the aqueous organic solvent, the method of removing the precipitate is chosen in view of various criteria including extractability of the polysorbate bound to the physiologically active protein using the aqueous organic solvent, high absorbance ratio, ease of implementation, small errors and high reproducibility. Filtration or centrifugation is preferred, and centrifugation is more preferred.

Embodiment B

Another preferred embodiment of the invention is characterized in that a proteolytic enzyme is added to the sample containing a physiologically active protein, thereby digesting the physiologically active protein, and thereafter the CoSCN reagent is added to the sample.

Therefore, in a preferred embodiment of the invention, the following steps are included:
1) adding a proteolytic enzyme to the sample containing a physiologically active protein, thereby digesting the physiologically active protein;
2) adding the CoSCN reagent to the sample obtained in 1);
3) adding a non-aqueous organic solvent to the sample and shaking the mixture;
4) collecting the obtained non-aqueous organic solvent layer and quantifying the cobalt thiocyanate complex by absorbance measurement; and
5) calculating the amount of the ethylene oxide based nonionic surfactant from the amount of the cobalt thiocyanate complex.

The proteolytic enzymes include proteinase K, pepsin, pancreatin, etc., with proteinase K being preferred. The amount of added proteolytic enzyme can be determined appropriately depending on the amount of the protein contained in the sample.

Embodiment C

In yet another embodiment of the invention, a protein included in the sample containing the physiologically active protein is added to a standard solution at the same concentration as in the sample, and a standard curve is constructed.

Therefore, in a preferred embodiment of the invention, the following steps are included:
1) adding the CoSCN reagent to the sample containing a physiologically active protein;
2) adding a non-aqueous organic solvent to the sample and shaking the mixture;
3) collecting the obtained non-aqueous organic solvent layer and quantifying the cobalt thiocyanate complex by absorbance measurement;
4) adding to a standard solution a protein included in the sample containing the physiologically active protein at the same concentration as in the sample, constructing a standard curve, and correcting on the basis of said standard curve the amount of the cobalt thiocyanate complex in the sample as obtained in 3); and
5) calculating the amount of the ethylene oxide based nonionic surfactant from the amount of the cobalt thiocyanate complex.

The method of the invention is preferred when the sample containing a physiologically active protein is a concentrated protein formulation and it is particularly preferred when the physiologically active protein is contained in the sample in an amount of at least 8 µg/ml.

Examples of the physiologically active protein contained in the sample to be measured by the method of the invention include but are not limited to hemopoietic factors such as a granulocyte colony stimulating factor (G-CSF), a granulocyte macrophage colony stimulating factor (GM-CSF), erythropoietin (EPO) and thrombopoietin, cytokines such as interferons, IL-1 and IL-6, monoclonal antibodies, tissue plasminogen activating factor (TPA), urokinase, serum albumin, blood coagulation factor VIII, leptin, insulin and stem cell growth factor (SCF). Among those proteins, hemopoietic factors such as EPO, G-CSF and thrombopoietin, as well as monoclonal antibodies are preferred, with EPO, G-CSF and monoclonal antibodies being more preferred.

The physiologically active protein has substantially the same biological activity as the physiologically active proteins in mammals, in particular, man and includes those which originate in nature as well as those which are obtained by gene recombination, with the latter being preferred. Proteins obtained by gene recombination include those having the same amino acid sequences as natural proteins, or those having one or more deletions, substitutions or additions of said amino acid sequences and which have said biological activity. The physiologically active protein further includes those which are chemically modified by PEG and the like.

Particularly preferred physiologically active proteins are proteins having sugar chains. The origin of sugar chains is not particularly limited but those which are added by mammalian cells are preferred. Exemplary mammalian cells include Chinese hamster ovary cells (CHO cells), BHK cells, COS cells and human-derived cells and among these, CHO cells are most preferred.

In the case where the physiologically active protein is EPO, the latter may be produced by any methods and EPOs that can be used include those which were extracted by various methods from human urine, then separated and purified, as well as those which were produced in Chinese hamster ovary cells (CHO), BHK cells, COS cells, human-derived cells, etc. by genetic engineering techniques (for example, JP 61-12288 A), extracted by various methods, then separated and purified. Also included are EPOs chemically modified by PEG, etc. (see International Patent Publication WO 90/12874). Also included are EPOs that have no sugar chains but which were chemically modified with PEG and the like. Further included are EPO analogs having the amino acid sequence of EPO modified such that the number of glycosylated sites, which are N-linked carbohydrate chain binding sites or O-linked carbohydrate chain binding sites, is increased by one or more (see, for example, JP 8-151398 A and JP 8-506023 A). Further, the number of sugar chain binding sites may-not be changed but the amount of sugar chains may be increased by increasing the content of sialic acid or the like.

In the case where the physiologically active protein is G-CSF, all kinds of G-CSF may be used as long as they have been refined to high purity. G-CSF to be used in the invention may be produced by any methods and include the following: a cell line of human tumor cells is cultured and G-CSF is extracted from the culture by various methods, then separated and purified; alternatively, G-CSF is produced by genetic engineering techniques in bacteria such as $E.\ coli$, yeasts, or animal-derived cultured cells such as Chinese hamster ovary (CHO) cells, C127 cells and COS cells, extracted by various methods, then separated and purified. Preferably, G-CSF is produced from $E.\ coli$, yeasts or CHO cells by genetic recombination. Most preferably, G-CSF is produced from CHO cells by gene recombination. Also included is G-CSF chemically modified with PEG, etc. (see International Patent Publication WO 90/12874).

When the physiologically active protein is an antibody, the latter may be polyclonal or monoclonal, and monoclonal antibodies are preferred. Monoclonal antibodies may be produced by any methods. Known technologies are basically employed to produce monoclonal antibodies; sensitizing antigens are immunized in accordance with common methods of immunization, the resulting immunocytes are fused to known parent cells by common cell fusion methods, and monoclonal antibody-producing cells are chosen by common screening methods. The monoclonal antibodies are not limited to those produced by hybridomas but include chimeric antibodies artificially modified with a view to lowering the characteristics as heteroantigen to human. Alternatively, reshaped human antibodies may be employed in the present invention. They have the complementarity determining region of an antibody of a mammal other than man such as a mouse antibody, which is substituted for the complementarity determining region of a human antibody, and applicable common gene recombinant techniques are also known. Reshaped humanized antibodies can be obtained by employing such known methods.

If required, amino acids in the framework (FR) region of the variable region of a reshaped human antibody may be replaced such that its complementarity determining region will form an appropriate antigen binding site (Sato et al., Cancer Res. 53:1-6, 1993). Such reshaped human antibody is preferably exemplified by humanized anti-IL-6 receptor antibody (hPM-1) (see International Patent Publication WO 92/19759).

In the sample containing a physiologically active protein which is to be measured by the method of the invention, a protein such as human serum albumin or purified gelatin may be contained as a stabilizer, but the sample is preferably substantially free of such proteins. However, even in the case where such proteins are contained as stabilizers, the polysorbate can appropriately be quantified by the method of the invention, particularly by employing the above-described embodiment C). More specifically, if a protein such as human serum albumin is contained as a stabilizer in the sample containing a physiologically active protein, the polysorbate can be quantified accurately by adding human serum albumin of the same concentration to a standard solution, constructing a standard curve, and correcting the amount of the cobalt thiocyanate complex in the sample on the basis of said standard curve.

If the sample containing a physiologically active protein is a protein formulation, its pH is preferably 4-8, more preferably 6.0-7.5. It should however be noted that the pH varies with the protein contained in the sample and is not limited to the values set forth above. For example, in the case of G-CSF, the pH is preferably 5-7, more preferably 6.0-6.7, and even more preferably 6.5. In the case of EPO, the preferred pH is 5-8 and the more preferred pH is 5.5-7.0. In the case of hPM-1 antibody, the preferred pH is 5.0-7.5.

When the sample containing a physiologically active protein is a protein formulation, the amount of the protein contained in the sample can be determined in accordance with the protein used, the type of the disease to be treated, the severity of the patient, the age of the patient, etc. Generally, the protein is contained in an amount of at least 0.01 µg/ml, preferably at least 0.1 µg/ml, more preferably at least 1 µg/ml. For example, in the case of EPO, the protein content is generally 100-500000 IU/ml, preferably 200-100000 IU/ml, more preferably 750-72000 IU/ml; in the case of G-CSF, the value is generally 1-1000 µg/ml, preferably 10-800 µg/ml, more preferably 50-500 µg/ml. In the case of an antibody, the value is generally 0.1-200 mg/ml, preferably 1-120 mg/ml.

The present invention further provides a method of quantifying an additive in a sample containing a physiologically active protein by adding a colorimetric reagent to the sample and quantifying by absorbance measurement the product formed between the colorimetric reagent and the additive in the sample containing a physiologically active protein, further including any one of the following steps:

A) adding an aqueous organic solvent to the sample containing a physiologically active protein, thereby forming a precipitate of the physiologically active protein, removing said precipitate, and thereafter adding the calorimetric reagent to the cleared sample;

B) adding a proteolytic enzyme, thereby decomposing the protein in the sample, and thereafter adding the calorimetric reagent; or C) adding to a standard solution a protein of the same kind in the same amount as the protein contained in the sample and constructing a standard curve.

Additives that can be measured by the above-described method of the invention include isotonization agents, diluents, solvent promoters, vehicles, pH adjusting agents, analgesic agents, buffers, sulfur-containing reducing agents and antioxidants. Isotonization agents include polyethylene glycol, as well as sugars such as dextran, mannitol, sorbitol, inositol, glucose, fructose, lactose, xylose, mannose, maltose, sucrose and raffinose; sulfur-containing reducing agents include, for example, compounds having a sulfhydryl group as exemplified by N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, thioalkanoic acids having 1-7 carbon atoms, etc. Antioxidants include chelating agents such as erysorbic acid, dibutylhydroxytoluene, butylhydroxyanisole, α-tocopherol, tocopherol acetate, L-ascorbic acid and salts thereof, L-ascorbyl palmitate, L-ascorbyl stearate, sodium hydrogensulfite, sodium sulfite, triamyl gallate, propyl gallate or ethylenediamine tetraacetic acid disodium (EDTA), sodium pyrophosphate, sodium metaphosphate, etc.

The amounts of these additives can be determined by a method including either one of the above-mentioned steps A), B) or C) in accordance with the known colorimetry.

The invention is described in greater detail by means of the following examples, to which the scope of the invention is by no means limited. Various alterations and modifications can be made by skilled artisans on the basis of the teachings of the invention and such alterations and modifications are also included within the invention.

Industrial Applicability

By using the method of the invention, the contents of ethylene oxide based nonionic surfactants in protein containing solution samples can be determined in a simple and accurate manner.

EXAMPLES

CoSCN Solution

| Ammonium thiocyanate | 17.4 g |
|---|---|
| Cobalt nitrate hexahydrate | 2.8 g |

These ingredients were dissolved in 100 mL of water.

Example 1

Quantitation of Polysorbate 20 in rG-CSF Injection

Preparing Standard Solutions and Sample Solutions

Standard solutions of polysorbate 20: Polysorbate 20 was dissolved in water to prepare solutions containing 0, 0.25, 0.5, 0.75 and 1.0 mg of polysorbate 20 in 2 ml of water. Those solutions were used as standard solutions of polysorbate. To 2 ml portions of those solutions, 25% human serum albumin (HSA) solution was added in 0.02 ml to prepare standard solutions.

Sample solutions of rG-CSF injection: An rG-CSF injection (containing 250 µg of recombinant G-CSF: Chugai Pharmaceutical) was put into 5 vials and 0.4 ml of water was added to each vial. The resulting solutions were combined to make a sample solution. Note that the sample solution of rG-CSF injection contained human serum albumin (HAS) as a stabilizer in an amount of about 1 mg per vial.

Standard Procedure

To a 2 ml portion of each standard solution or sample solution, 2 ml of a CoSCN solution was added and the mixture was shaken for 3 minutes (250 shakes/min). After adding 0.4 g of potassium chloride and 5 ml of water-saturated dichloromethane, the mixture was shaken for 10 minutes (250 shakes/min). By centrifugation at 3000 rpm for 30 minutes, the dichloromethane layer (bottom layer) was collected, and absorptiometry was performed to measure OD at 320 nm.

(1) Absorption Spectra of Polysorbate 20-CoSCN Combined Complex

A standard solution of polysorbate 20 (0.5 mg/2 ml), the sample solution or water (blank) was mixed with a CoSCN reagent in accordance with the standard procedure. FIG. 1 shows absorption spectra (250-700 nm) for the dichloromethane layers obtained.

The standard solution and the sample solution had no differences in absorption spectrum and both showed absorption maxima at 320 nm and 620 nm. Those were absorptions attributed to the combined complex of polysorbate 20 and CoSCN. The blank did not show any maximum absorption in those wavelength ranges, except having a slight absorption at 320 nm (OD<0.10).

(2) Investigation of Extracting Organic Solvents

The standard solutions of polysorbate 20 (0-1 mg) were treated in accordance with the standard procedure and absorption spectra were measured, except that the samples were extracted with 1,2-dichloroethane, chloroform, toluene and benzene, rather than with dichloromethane. None of them had differences in absorption maxima at around 320 nm and 620 nm, and there was no spectral change due to the solvent species. Therefore, it was decided to perform quantitation using the absorption at 320 nm allowing for the greater absorbance.

Next, calibration lines were constructed from the same standard solutions of polysorbate 20 with using the above-noted solvents as extraction solvents, and the detection intensities of the combined complex in the respective solvents were compared. Those solvents were used after being mixed with water in a separating funnel and separated as water-saturated masses. The results were as follows: dichloromethane and 1,2-dichloroethane showed comparable absorption intensities, with chloroform showing about two thirds of those intensities whereas the intensities for toluene and benzene were no more than a tenth. Therefore, from the viewpoint of measurement intensity, dichloromethane and 1,2-dichloroethane were found to be suitable solvents.

Organic solvents, in particular, halogen-containing organic solvents are known to cause irreversible precipitation of proteins with which they were mixed. The rG-CSF injection contains not only rG-CSF but also HSA, and the protein precipitates incorporate a portion of the complex upon extraction of the combined complex. Therefore, using three solvents, dichloromethane, 1,2-dichloroethane and chloroform, the effect of HSA (5 mg) on incorporation of the combined complex during extraction was investigated. The results are shown in Table 1.

TABLE 1

Comparison of recovery rates of the combined complex with extraction solvents in the presence of HSA

| Extraction solvent | Recovery rate of the combined complex (%) |
|---|---|
| 1,2-dichloroethane | 47.3 |
| dichloromethane | 73.1 |
| chloroform | 75.4 |

From the viewpoint of recovery rate, dichloromethane and chloroform are suitable. From the viewpoints of both measurement intensity and recovery rate, dichloromethane was found to be suitable as an extraction solvent.

(3) Amount of Added CoSCN Reagent

An investigation was made of the amount of the CoSCN reagent that was required for the reaction of forming a combined complex with 1 mg of polysorbate 20. As it turned out, the reaction proceeded completely with 2 ml or more of the reagent, rendering the reagent excessive. Since the rG-CSF injection contained 0.5 mg of polysorbate 20, 2 ml of the reagent was found to be adequate.

(4) Relationship Between the Reaction Time and Detection Intensity for the Combined Complex An investigation was made of the relationship between the time of reaction, which is caused by shaking 0.5 mg of polysorbate 20 and the CoSCN reagent, and the detection intensity of the resulting combined complex. As it turned out, the reaction had ended completely by shaking for at least one minute. Hence, the time of reaction with the reagent was set at 3 minutes.

(5) Relationship Between the Combined Complex and the Volume of Sample Solution

Figure 2:
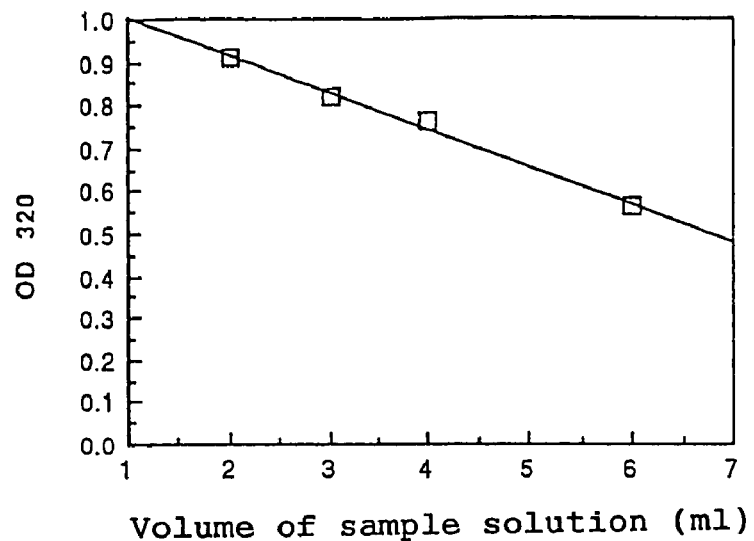
FIG. 2 is a graph showing the relationship between the detection intensity of a combined complex and the volume of the sample solution.

Since the combined complex of polysorbate 20 and the CoSCN reagent is quantified after extracting the combined complex, it is anticipated that the efficiency of extraction will vary with the volume of the reagent solution. Solutions having 0.5 mg of polysorbate 20 dissolved in 2, 3, 4 and 6 ml of water were treated similarly, and the detection intensities of the combined complex were compared. As FIG. 2 shows, the detection intensity differed with the volume of the sample solution. Therefore, the volume of the standard solution had to be the same as that of the sample solution and 2 ml was used throughout.

(6) Effect of Salting Out

Figure 3:
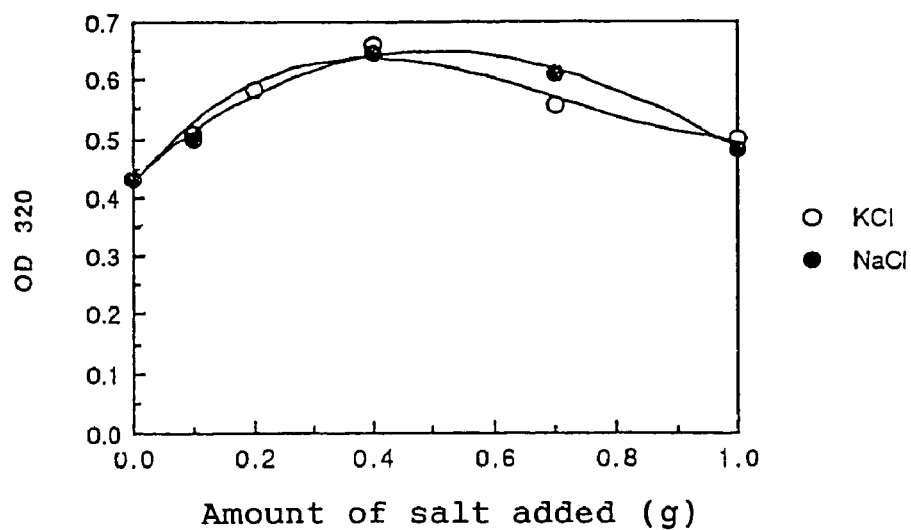
FIG. 3 shows the effect of salting out on 2 ml of the standard solution (0.5 mg/2 ml) in the case of using potassium chloride and sodium chloride.

FIG. 3 shows the effect of salting out on 2 ml of the standard solution (0.5 mg/2 ml) in the case of using potassium chloride or sodium chloride as a salt. Whether potassium chloride or sodium chloride was used, the absorbance increased with the increasing the amount of addition, and had a maximum at 0.4 g. Beyond 0.7 g, poor separation occurred and the efficiency decreased again. There was little difference between potassium chloride and sodium chloride.

(7) Relationship Between the Amounts of Other Vehicles (HSA, Mannitol and Phosphate) or rG-CSF and the Detection Intensity of the Complex An investigation was made of the effect the amount of addition of HSA, mannitol, phosphate (mixture of Na$_2$HPO$_4$—NaH$_2$PO$_4$.2H$_2$O) or rG-CSF would have on 2 ml of the standard solution (0.5 mg/2 ml).

The absorption intensity of HSA decreased with the increasing amount of addition, and was constant in a range of 3-10 mg where the absorption intensity decreased by about 20% from the initial value. Mannitol did not show any remarkable effect when it was in amounts of up to 0.5 g. The phosphate-did not show any significant effect when it was added in amounts of up to 20 mg. The rG-CSF did not show any detectable effect when it was added in amounts of up to 2 mg.

(8) Reaction Between the Reagent and Other Vehicles (HSA, Mannitol and Phosphate) or rG-CSF, and Their Extraction Into the Dichloromethane Layer The reactivity between the CoSCN reagent and HSA (5 mg), mannitol (250 mg), phosphate (32 mg) or rG-CSF (1.25 mg) contained in 5 vials of the rG-CSF injection and their extraction into dichloromethane were investigated, and the results are shown in Table 2.

TABLE 2

|  | OD 320 nm |
| --- | --- |
| blank | 0.064 |
| HSA (5 mg) | 0.056 |
| mannitol (250 mg) | 0.056 |
| phosphate (32 mg) | 0.048 |
| rG-CSF (1.25 mg) | 0.052 |

As is clear from Table 2, the absorption intensities in the dichloromethane solutions did not show any detectable differences from the blank value, thus verifying that the reaction products between the CoSCN reagent and the tested vehicles or rG-CSF showed no absorption.

(9) Deproteinization of Sample Solution

As described in (7) above, the recovery rate of the combined complex during extraction decreases on account of the HSA in the sample. An investigation was therefore made to develop a method by which only the protein in the sample solution could be removed effectively. Deproteinization must satisfy the following conditions:
a) polysorbate 20 should be kept intact without being impaired by the treatment;
b) the treated sample solution should have such a composition that it will not interfere with the reaction with the CoSCN reagent;
c) the volume of the sample solution should not be increased so that the extraction efficiency of the complex is not lowered;
d) the operation should be simple;
e) the treatment should not lower the reproducibility of the quantified values.

Considering these, the inventors made attempts at treatment with a solid phase in a reverse-phase system (treatment with Sep-Pack C18 or Sep-Pack CN), separation with an ultrafiltration membrane, deproteinization by salting out, protein denaturation and precipitation by addition of ethanol, protein precipitation and separation with trichloroacetic acid, and none of them were able to remove only proteins with high efficiency. Therefore, the inventors decide not to remove the protein in the sample solution but to add HSA to the standard solution so that the extraction rate would correspond to that of the sample solution.

(10) Detection Intensity of the Combined Complex and the Effect of pH of the Reaction Solution To each of the sample and standard solutions, the CoSCN reagent was added to make reaction solutions. By actual pH measurements, a value of about 5.8 was obtained with the sample solution and about 5.4 with the standard solutions (no difference was detected between the sample solutions within the range of 0-1.0 mg/2 ml). Check was made to see whether the difference between the pH values of 5.4 and 5.8 would have any effect on the reactivity with the reagent.

A standard solution (0.5 mg/2 ml) was made from a phosphate buffer at a concentration of $5 \times 10^{-3}$ M, and the CoSCN reagent was added to make reaction solutions with pH in a range from 2.6 to 6.2. As a result, the absorption intensity was constant at pH of 5.2 and above, verifying that the difference in pH between the sample and standard solutions did not have any effect on the reaction.

(11) Extraction Rate of the Combined Complex with Dichloromethane

It was determined what percentage of combined complex, which was produced by reaction from the sample solution or the standard solution, could be extracted into the dichloromethane layer in a single run. Extractions were repeated for three times, and the percentage of the combined complex obtained by the first run was calculated on the basis of the quantified values of the combined complex as extracted into the dichloromethane layer in the respective runs. The results are shown in Table 3.

TABLE 3

| Extraction rate of the combined complex with dichloromethane (n = 3 in each run) | | | |
| --- | --- | --- | --- |
|  | Extraction rate of the combined complex | | |
|  | 1st run | 2nd run | 3rd run |
| standard solution | 91.5% | 5.7% | 2.8% |
| sample solution | 91.8% | 7.7% | 0.5% |

As is clear from the table, about 92% extraction was achieved in both the standard and sample solutions, verifying that there was no difference between the standard and sample solutions.

(12) Calibration Curves

Calibration curves were constructed from three standard solutions, one having 5 mg of HSA added to the standard solutions of polysorbate 20 (0-1 mg/2 ml) and hereunder designated as B, another having 5 mg of HSA and 250 mg of mannitol added to those standard polysorbate solutions and hereunder designated as C, and the third having no compound added to the standard polysorbate solution and hereunder designated as A. In consequence, good linearity was obtained over the range of 0-1 mg of polysorbate 20, with passing near the zero point. It should however be noted that the recovery rate of the combined complex decreased in B and C (see above) and the absorption intensity was about 80% of the value for A, with no difference observed between B and C. Therefore, with a view to matching with the extraction rate of the combined complex from the sample solution, the calibration line for the condition of B was adopted.

The adopted calibration curve had a linear regression coefficient of $r \geqq 0.99$ that was determined on the basis of the result for n=7.

(13) Quantitation Limit

From the result of measurement of the blank value using water, the quantitation limit was about 0.01 mg/vial.

(14) Recovery Rate of Polysorbate 20

Recovery rate was determined for the case where polysorbate was added to the rG-CSF injection in amounts of 0.02-0.10 mg per vial. For recovery rate calculation, the total amount of polysorbate 20 in the samples made by adding the standard solutions to the rG-CSF injection was determined, and the amount of polysorbate 20 initially contained in the rG-CSF injection (0.095 mg/vial) was subtracted from that total amount. As a result, about 100% was exhibited when polysorbate 20 was added in amounts of 0.04 mg/ml and higher. Therefore, it was concluded that polysorbate 20 in the sample could be quantified at recovery rate of 100% by the quantitation method of the invention.

(17) Actual Measurement on rG-CSF Injection

Using 17 lots of the rG-CSF injection (Chugai Pharmaceutical: 5 vials each for 15 lots and 3 vials each for 2 lots), the contents of polysorbate 20 were actually measured. Absorption spectra were also measured.

In all lots, the content of polysorbate 20 was 0.095-0.108 mg/vial, showing that values were in substantial agreement with the notated value (0.1 mg/vial). In each lot, the absorption spectra of the combined complex showed absorption maxima at 317-319 nm and 619-622 nm, thus lot-to-lot differences were not detected.

Example 2

Quantitation of Polysorbate 80 in hPM-1 (Humanized Anti-IL-6 Receptor Antibody) Containing Samples (Removal of hPM-1 by Addition of Acetone)

Formulation of Samples

To prepare an hPM-1 (humanized anti-IL-6 receptor antibody) solution, a stock solution of hPM-1 (Chugai Pharmaceutical) was concentrated by ultrafiltration until the concentration of hPM-1 reached 33 mg/mL (ca. 19 mM sodium phosphate buffer, ca. 190 mM NaCl, pH 6.6).

As a placebo solution, a 15 mM sodium phosphate buffer containing 120 mM sodium chloride (pH 6.6) was prepared.

(1) Dependency on the Concentrations of Polysorbate 80 and hPM-1 as Determined by Acetone Precipitation Method A 2.5-ml of hPM-1 solution (at a concentration of 20 mg/ml or 40 mg/ml) containing polysorbate 80 (at a concentration of 0.005% or 0.01%) was prepared. To each of those solutions, 4 ml of acetone was added, shaken for 20 minutes, and then centrifugation was performed for 10 minutes (3000 rpm) to remove the precipitate. An additional 4 ml of acetone was added to the precipitate, and the mixture was shaken and centrifuged; these procedures were repeated twice and the supernatants obtained in the respective runs were combined, put into an eggplant type flask, and evaporated to dryness. To the residue, 2.5 ml of water was added to redissolve it, and 2 ml was taken as a sample solution. To the sample solution, 2 ml of the CoSCN reagent and 0.5 g of potassium chloride were added and the mixture was shaken for 3 minutes; 2 ml of dichloromethane was then added and the mixture was shaken for 10 minutes. The bottom layer was recovered and the absorbance at 320 nm was measured. Separately, the placebo solution was treated similarly and the absorbance was measured to determine the absorbance ratio between the sample solution and the placebo. The results are shown in Table 4.

TABLE 4

| | Absorbance ratio as determined by acetone precipitation | | | |
|---|---|---|---|---|
| Concentration of polysorbate 80 | 0.005% | | 0.01% | |
| Concentration of hPM-1 (mg/mL) | 20 | 40 | 20 | 40 |
| absorbance ratio (%) | 77.63 | 93.64 | 93.68 | 110.18 |

Thus, even when the concentration of hPM-1 was elevated to 20 mg/mL or 40 mg/mL, the recovery rate was comparatively higher than in the case of the placebo. Recovery rate was also suggested to be independent of the concentration of hPM-1.

(2) Investigation of Methods for Removing the Precipitate

As tools for use in filtering the precipitate formed by addition of acetone, a Kiriyama funnel and filter holders, which differed in the area of filtration or the tool's surface area, were chosen and subjected to experimentation. The results are summarized in Table 5 below together with the result of centrifugation.

TABLE 5

| | | | Summary of various methods of separation by acetone precipitation | | | | |
|---|---|---|---|---|---|---|---|
| | | | Advantage | Disadvantage | Absorbance ratio (%) | CV (%) | Rating |
| filtration | Filter holders | φ47 mm | Easy to handle | The precipitate is difficult to wash. | 101 | 10 | ○ |
| | | φ25 mm | Fewer sample transfers | Clogging is easy to occur | 84 | 18 | X |
| | | φ25 mm (3 mL) | contributed to reducing errors. | | 72 | 13 | X |
| | Kiriyama funnel | | Having smaller surface areas than other tools. | The precipitate is difficult to wash. Clogging is easy to occur. The precipitate would spill from over the edge of the filter paper. | 88 | 26 | X |

TABLE 5-continued

Summary of various methods of separation by acetone precipitation

| | Advantage | Disadvantage | Absorbance ratio (%) | CV (%) | Rating |
|---|---|---|---|---|---|
| Centrifugation | The precipitate is highly washable and hence is easy to extract. | Time-consuming due to many sample transfers | 104 | 5 | ◎ |

In short, precipitation and separation by filtration features high operational efficiency but on the other hand polysorbate 80, presumably having adsorbed on the precipitate, could not be thoroughly washed off. The more likely a method is to experience clogging, the greater the tendency of the absorbance ratio to decrease. Therefore, it was concluded that filtration was not suitable as a method of quantifying polysorbate 80.

In contrast, centrifugation involved many sample transfers and hence had a tendency to require prolonged measurement. However, polysorbate 80, presumably having adsorbed on the precipitate, could be thoroughly extracted, the absorbance ratio was almost 100%, and the variation in the measurement was small.

(3) Investigating the Effect of Salting-out

There is a tendency for CV to increase with decreasing absorbance, so in order to achieve consistent absorbance values that would involve small errors, an investigation was made of the addition of salts.

First, in order to investigate the optimization of the amount of added potassium chloride, 2 mL of a placebo solution of 0.01% polysorbate 80 was treated by the standard procedure, and absorbance measurements were performed. The absorbance increased as the amount of added KCl was increased, and the slope started to decrease at about 0.5 g. Therefore, the amount of addition of KCl was set at 0.5 g.

In the next place, the reproducibility of KCl addition was evaluated. For both hPM-1 and placebo, 2 mL of a solution of 0.01% polysorbate 80 was centrifuged to prepare a solution (2 mL) which was then treated by the standard procedure for absorbance measurements. The experiment was conducted for n=5 and the duration was 2 days. The results were evaluated for within-day and day-to-day differences, as shown in Table 6 below.

TABLE 6

Within-day and day-to-day differences in absorbance measurements using the effect of salting out

| | Placebo | hPM-1 | | Placebo | hPM1-1 |
|---|---|---|---|---|---|
| Absorbance | 0.4345 | 0.3998 | Absorbance | 0.4431 | 0.4323 |
| | 0.4379 | 0.4246 | | 0.4434 | 0.4323 |
| | 0.4381 | 0.4433 | | 0.4401 | 0.4461 |
| | 0.4603 | 0.4574 | | 0.4463 | 0.4290 |
| | 0.4353 | 0.4495 | | 0.4576 | 0.4276 |
| Average | 0.4412 | 0.4349 | Average | 0.4461 | 0.4335 |
| CV | 2.4437 | 5.3034 | CV | 1.5228 | 1.6980 |
| Recovery rate after addition (%) | | 98.57 | Recovery rate after addition (%) | | 97.17 |

Looking at the placebo/hPM-1 ratio (%), it was satisfactory on both the first and the second day (98.57% and 97.17%). The variation was about 5% and may well be described as acceptable. It was therefore found that the addition of KCl improved both the variation and the recovery rate.

(4) Accuracy and Repeatability

By the test method as set on the basis of the investigations (1)-(3), the hPM-1 solution containing 0.05% polysorbate 80 was measured. The recovery of polysorbate 80 was 99.8% and the coefficient of variation was 7.6%; thus, good results were obtained in both accuracy and coefficients of variation (CV).

TABLE 7

| No. | Concentration of polysorbate 80 (%) | Recovery rate (%) |
|---|---|---|
| 1 | 0.0520 | 102.7 |
| 2 | 0.0527 | 104.1 |
| 3 | 0.0526 | 103.9 |
| 4 | 0.0447 | 88.4 |
| Mean recovery rate (%) | | 99.8 |
| Standard deviation of recovery rate | | 7.59 |
| 95% confidence interval of recovery rate | | 7.6 |

Example 3

Quantitation of Polysorbate 80 in EPO Injection (Protein Decomposition With Proteinase K)

Samples

An EPO active substance solution, an EPO solution formulation (containing 750 units of EPO) and another EPO solution formulation (containing 24000 units of EPO) were all produced by Chugai Pharmaceutical. Each of those EPO formulations contained 0.005% of polysorbate 80.

Proteinase K Solution

To 100 mg of proteinase K (Wako Pure Chemical), TE (pH 8.0) (Wako Pure Chemical) was added to make 50 ml, thereby preparing a solution containing 2 mg/ml of proteinase K.

Standard Procedure

To 2 ml of the sample solution, 2 ml of a solution of the CoSCN reagent was added and the mixture was stirred for 3 minutes. After addition of potassium chloride (0.4 g), 1 ml of dichloromethane (water saturated) was added and the mixture was stirred for 10 minutes. After 30-minutes centrifugation at 3000 rpm, the dichloromethane layer (bottom layer) was collected and OD at 320±2 nm was measured by absorbance measurement method.

(1) Selection of Extraction Solvents

Extraction rate of polysorbate 80 differs with the extraction solvent used. Therefore, an investigation was made using dichloromethane and chloroform as extraction solvents. Using 2 ml of an aqueous solution of 0.005% polysorbate 80, the OD at 320±2 nm of the extraction solvent layer was measured in accordance with the standard procedure. As it turned out, a higher absorbance was obtained from extraction with dichloromethane than with chloroform.

When the same procedure was performed with water as the sample, no particularly interfering spectra were detected whichever solvent was used. Therefore, dichloromethane providing the higher absorbance was chosen as the extraction solvent.

(2) Investigating the Reaction of the Combined Complex and the Volume of the Co SCN Reagent's Solution An investigation was made of the volume of the CoSCN reagent's solution that allowed for quantitation of polysorbate 80 over the concentration range of 0-0.010%. To 0.4 ml of an aqueous solution of 0.050% polysorbate 80, 3.6, 3.1, 2.6, 1.6, 0.6 or 0 ml of water was added, to the respective aqueous solutions the CoSCN reagent's solution was added in amounts of 0, 0.5, 1.0, 2.0, 3.0 and 4.0 ml to make a total of 4.0 ml, and measurements were conducted in accordance with the standard procedure. As it turned out, the absorbance increased as the volume of the reagent's solution increased, and the reaction curve (absorbance) substantially leveled off at 2 ml and above. In view of the intended range of quantitation, 2 ml was found to be sufficient as the volume of the reagent's solution.

(3) Investigating the Reaction Time for the Formation of the Combined Complex

An investigation was made of the reaction time required for polysorbate 80 in the sample to react completely with the CoSCN reagent's solution to form the combined complex. Using 2 ml of an aqueous solution of 0.005% polysorbate 80 as the sample. and setting the reaction time at 0, 1, 2, 3 or 5 min, OD at 320±2 nm was measured in accordance with the standard procedure. There was no substantial difference in absorbance for these measurements at the reaction times, and thus the reaction was believed to progress rapidly.

(4) Investigating the Amount of Dichloromethane

An investigation was made of the amount of dichloromethane required to extract the combined complex. Using 2 ml of an aqueous solution of 0.005% polysorbate 80, the amount of dichloromethane to be added was set at 1.0, 2.0 and 3.0 ml, and OD at 320±20 nm was measured in accordance with the standard procedure. As a result, when the amount of dichloromethane was doubled and tripled, the absorbance decreased to about a half and a third. It was therefore considered that the amount of dichloromethane would hardly affect the partition ratio.

(5) Investigating the Effect of Salting Out

An investigation was made of the effect of salting out in the case of extracting the combined complex with dichloromethane. Using 2 ml of an aqueous solution of 0.005% polysorbate 80 as the sample, potassium chloride was added in amounts of 0.0, 0.2, 0.4, 0.6 and 0.8 g, and OD at 320±2 nm was measured in accordance with the standard procedure. As it turned out, the absorbance increased with the increasing the amount of added potassium chloride, and substantially leveled off at 0.4 g and above.

(6) Evaluating the Method of Deproteinization

As noted in Example 1, the extraction rate of the combined complex was observed to decrease when a protein was present in the sample. As a matter of fact, for the most concentrated EPO formulation containing about 400 µg/ml of EPO, the extraction rate of the combined complex decreased to about 70%. In addition, in view of the broad dose range of EPO formulations (0.8 µg/ml-400 µg/ml), it was anticipated that the absorbance obtained would also vary with the dose.

A need therefore arose to effectively remove the protein (EPO) from the sample solution. In this case, the method of deproteinization must satisfy the conditions noted in Example 1(9).

Considering these, the following method was tried.

Protein digestion with proteinase K; From samples of different protein contents (an aqueous solution of 0.005% polysorbate 80 (blank), EPO 750 IU/0.5 ml, EPO 24000 IU/0.5 ml), substantially identical absorbance values were obtained, and it was found that no decrease due to the protein occurred in the recovery rate of the combined complex.

It was therefore considered effective to perform protein digestion using proteinase K.

(7) Effects of Protein Content

The protein content was varied and the possible effect on quantitation was investigated. Using 2 ml each of aqueous solutions of 0.0025-0.010% polysorbate 80 containing 1500, 48000 and 72000 IU/ml of EPO, measurements were conducted in accordance with the test method. As it turned out, there was no difference in absorbance for the concentrations of polysorbate 80, and it was verified that the step of protein digestion did not cause any effect of the protein content on quantitation.

(8) Linearity of Calibration Curves

Standard solutions of polysorbate 80 at 0, 0.001, 0.0025, 0.005, 0.0075 and 0.01% were measured in accordance with the test method and calibration curves were constructed. As it turned out, all calibration curves had a correlation coefficient of $r \geq 0.999$, indicating that the lines approximately passed the zero point.

(9) Intermediate Precision and Accuracy

Aqueous solutions of polysorbate 80 at 0.0025, 0.0050 and 0.0100% were measured in accordance with the test method. As it turned out, the aqueous solutions of 0.0025, 0.0050 and 0.0100% polysorbate 80 had coefficients of variation (C.V.) of 4.7, 5.2 and 4.7%, respectively. The accuracy was 102.7, 99.4 or 101.2%, respectively. The results were satisfactory in terms of both C.V. and accuracy.

As already noted, the coefficient of correlation obtained from the five-point calibration curves was so good that it was expected that both precision and accuracy would be secured. Hence, a comparison was made with the values of measurement obtained from the one-point calibration curves using an aqueous solution of 0.005% polysorbate 80; the results of measurement were C.V.=4.6% and trueness of 100±5.6%, verifying that there was no problem with precision and accuracy.

The invention claimed is:

1. A method of quantifying polysorbate in a sample containing a physiologically active protein, comprising:
adding an aqueous organic solvent to the sample containing a physiologically active protein, thereby forming a precipitate of the physiologically active protein,
removing the precipitate from the sample to thereby obtain a cleared sample, and
thereafter adding an ammonium thiocyanate/cobalt nitrate reagent (CoSCN reagent) to the cleared sample, thereby forming a resulting cobalt thiocyanate complex, to thereby obtain a sample containing the cobalt thiocyanate complex;

adding a non-aqueous organic solvent to the sample containing the cobalt thiocyanate complex to thereby obtaining a mixture of non-aqueous organic solvent and the sample containing the cobalt thiocyanate complex;

shaking the mixture to extract the cobalt thiocyanate complex into a non-aqueous organic solvent layer thereby obtaining a non-aqueous organic solvent layer containing the cobalt thiocyanate complex;

collecting the non-aqueous organic solvent layer containing the cobalt thiocyanate complex;

quantifying the cobalt thiocyanate complex in the non-aqueous organic solvent layer by absorbance measurement with a spectrophotometer by measuring absorbance at 320 nm; and quantifying polysorbate in the sample by calculating the amount of polysorbate from the amount of the cobalt thiocyanate complex.

2. The method according to claim 1, wherein the aqueous organic solvent is acetone.

3. The method according to claim 2, wherein the precipitate is removed by filtration or centrifugation.

4. The method according to claim 1, wherein the precipitate is removed by filtration or centrifugation.

5. The method according to claim 1, wherein the polysorbate is polysorbate 20 and/or 80.

6. The method according to claim 1, wherein the non-aqueous organic solvent is dichloromethane.

7. The method according to claim 1, wherein the sample containing the physiologically active protein is a concentrated protein formulation.

8. The method according to claim 7, wherein the physiologically active protein is contained in the sample in an amount of at least 8 μg/ml.

9. The method according to claim 7, wherein the physiologically active protein is a hemopoietic factor protein.

10. The method according to claim 9, wherein the physiologically active protein is erythropoietin.

11. The method according to claim 9, wherein the physiologically active protein is a granulocyte colony stimulating factor.

12. The method according to claim 1, wherein the physiologically active protein is an antibody.

* * * * *